United States Patent [19]

Bieron et al.

[11] Patent Number: 4,792,618

[45] Date of Patent: Dec. 20, 1988

[54] FLUORINATED CARBOCYLIC COMPOUNDS

[75] Inventors: Joseph F. Bieron, Tonawanda; David Y. Tang, E. Amherst, both of N.Y.

[73] Assignee: Occidental Chemical Corporation, Niagara Falls, N.Y.

[21] Appl. No.: 680,695

[22] Filed: Dec. 12, 1984

Related U.S. Application Data

[63] Continuation-in-part of Ser. No. 604,272, May 2, 1984, Pat. No. 4,517,372.

[51] Int. Cl.$^4$ .................. C07C 69/75; C07C 49/303; C07C 121/46; C07C 53/44
[52] U.S. Cl. .................. 560/127; 260/544 F; 260/544 L; 558/431; 560/1; 568/376; 568/831; 570/131; 570/186
[58] Field of Search ............ 260/544 F, 544 L, 464; 560/1, 127; 568/376, 831; 570/131, 186

[56] References Cited

U.S. PATENT DOCUMENTS

| | | | |
|---|---|---|---|
| 3,046,094 | 7/1962 | Arth et al. | 570/131 X |
| 3,093,692 | 6/1963 | Valkanas et al. | 570/131 X |
| 3,238,260 | 3/1966 | Pasedach et al. | 568/376 X |
| 3,306,724 | 2/1967 | Di Bella et al. | 570/186 X |
| 3,332,993 | 7/1967 | Nychka et al. | 260/544 F |
| 4,181,631 | 1/1980 | Shaffer et al. | 568/376 X |

OTHER PUBLICATIONS

Gilbert et al., *Chemical Abstracts*, vol. 44, Column 9363a–g, (1950).
Spassov et al., *Journal of the American Chemical Society*, vol. 89, No. 1, pp. 88–94, Jan. 4, 1967.
Stolow et al., *Chemical Abstracts*, vol. 75, 75986h, (1971).

Primary Examiner—Werren B. Lone
Assistant Examiner—Vera C. Clarke
Attorney, Agent, or Firm—James F. Tao; Arthur S. Cookfair

[57] ABSTRACT

Fluoro-substituted carbocyclic compounds are prepared by
(A) reacting hydrogen fluoride with a chlorocyclohexenyl compound of the formula

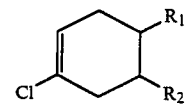

where $R_1$ and $R_2$ are independently selected from the group consisting of —H, —CH$_2$OH, —COF, —COCl, —CF$_3$, —CN,

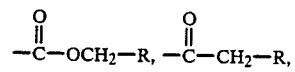

and —CH$_2$R, where R is —H or alkyl of 1–4 carbon atoms, to form a gem-dihalocyclohexane compound of the formula

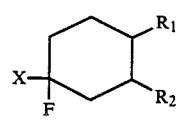

where X is chlorine and $R_1$ and $R_2$ are as defined above,
(B) dehydrohalogenating the gem-dihalocyclohexane compound in the vapor phase to form a fluorocyclohexenyl compound of the formula

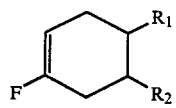

(C) contacting the fluoro-cyclohexenyl compound, in the vapor phase, with a dehydrogenation catalyst to form a fluoro-substituted aromatic compound of the formula

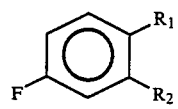

11 Claims, No Drawings

FLUORINATED CARBOCYLIC COMPOUNDS

CROSS-REFERENCE TO RELATED APPLICATIONS

This is a continuation-in-part of copending application Ser. No. 604,272, now U.S. Pat. No. 4,517,372.

BACKGROUND OF THE INVENTION

This invention relates to fluorinated carbocyclic compounds and to a method for the preparation thereof. The fluorinated carbocyclic compounds prepared in accordance with the invention include optionally substituted gem-dihalocyclohexane compounds, fluorocyclohexenyl compounds and fluoro aromatic compounds, useful as chemical intermediates for the synthesis of a wide variety of end products, especially for the synthesis of pesticides, pharmaceuticals and polymers. Thus, for example, the fluoroaromatic compounds are particularly useful in the synthesis of a wide variety of diphenyl ether herbicides and the like by reaction, in a known manner with an alkali metal phenoxide.

There are, at present, only a limited number of synthetic methods for producing fluorine substituted aromatic substrates, and these methods are generally not commercially attractive. See Max M. Boudakian, *Encyclopedia of Chemical Technology*, Kirk-Othmer 3rd Ed., Vol. 10, pp. 901-936. One method is the Schiemann reaction, in which a diazonium fluoroborate salt is decomposed, converting an aniline to a fluorobenzene derivative. On an industrial scale, substituted anilines are diazotized with sodium nitrite in anhydrous hydrogen fluoride, followed by in situ decomposition of the aryldiazonium fluoride. However, the reaction conditions, variable yields, and environmentally troublesome by-products present difficulties when this reaction is employed in a large scale commercial process.

Aromatic substrates with electron withdrawing groups can be reacted with fluoride ions to replace chlorine substituents and yield fluoroaromatic derivatives. These reactions are usually conducted under vigorous conditions and proceed by nucleophilic substitution with fluoride ions. The positional requirement for electron withdrawing substituents as well as special solvents and waste KF/KCl salts limits the synthetic utility of this type of reaction.

The common method of halogenating an aromatic substrate is by a Lewis acid catalyzed electrophilic substitution type reaction. There are numerous reagents suitable for bromination and chlorination but few available for fluorination. Molecular fluorine is much too reactive and results in poor selectivity in most reactions. The synthetic approach has been to design less reactive fluorinating agents, but each reagent has its drawbacks for commercial application.

The preparation of 1-fluorocycloalkene from the corresponding 1,1-difluorocycloalkane by reaction with anhydrous neutral alumina is disclosed in Strobach et al., *J. Org. Chem.*, Vol. 36, pages 818-820 (1971). The 1,1-difluorocycloalkane is prepared by reaction of the corresponding cyclic ketone and sulfur tetrafluorddie.

Hasek et al, *J. Amer. Chem. Soc.*, 82, 543 (1960) disclose the preparation of gem-difluorocycloalkanes by reaction of the corresponding cyclic ketone with sulfur tetrafluoride and hydrogen fluoride. Among the specific reactions disclosed in the reference is the reaction of cyclohexanone with sulfur tetrafluoride at temperatures below 50° Celsius to form 1,1-difluorocyclohexane.

The process of the present invention utilizes chlorocyclohexenyl compounds as starting reactants. The chlorocyclohexenyl compounds employed are, for the most part, known compounds, some of which are commercially available. These compounds may be conveniently prepared by a Dills-Alder reaction of a suitable diene, such as chloroprene, with various dienophiles. See, for example, I. Inukai and M, Kasai, J. Org. Chem. 30, 3567 (1965). The preparation of chlorocyclohexenyl compounds in this manner may be represented schematically by the following equation:

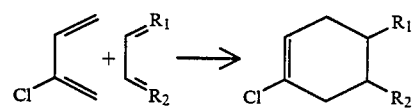

In the process of the present invention, the chlorocyclohexene starting reactant is converted to a gem-dihalo intermediate and then to a corresponding fluorocyclohexene intermediate. Some of the fluorocyclohexene intermediates are known compounds and have been shown in the literature to be prepared by means of a Diels-Alder reaction utilizing fluoroprene in the following manner. (A. A. Petrov and A. V. Tumanova CA 51 g)

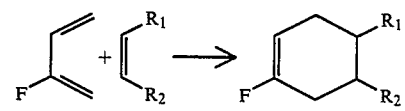

However, the making and handling of fluoroprene on a commercial scale presents serious difficulties, including explosion hazards, due to the unstable nature of fluoroprene. By the process of the present invention the difficulties and hazards associated with the making and handling of fluoroprene are avoided.

It is therefore an object of the present invention to provide a novel synthetic route for the preparation of mono- and di-substituted fluoro aromatic compounds. It is a further object of the invention to provide novel substituted fluorocarbocyclic intermediate compounds which can be used in the synthesis of substituted fluoroaromatic compounds.

SUMMARY OF THE INVENTION

In accordance with this invention, fluoro-substituted carbocyclic compounds are prepared by (A) reacting hydrogen fluoride with a chlorocyclohexenyl compound of the formula

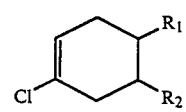

where $R_1$ and $R_2$ are independently selected from the group consisting of —H, —CH$_2$OH, —COF, —COCl, —CF$_3$, —CN,

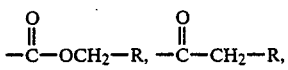

and —CH$_2$R, where R is —H or alkyl of 1-4 carbon atoms, to form a gem-dihalocyclohexane compound of the formula

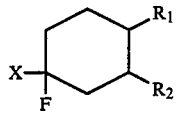

where X is chlorine or fluorine and R$_1$ and R$_2$ are as defined above, (B) dehydrohalogenating the gem-dihalocyclohexane compound in the vapor phase to form fluoro-cyclohexenyl compound of the formula

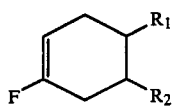

(C) and contacting the fluoro-cyclohexenyl compound, in the vapor phase, with a dehydrogenation catalyst to form a fluoro-substituted aromatic compound of the formula

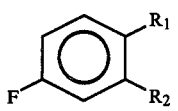

The preferred compounds employed in the process of this invention are those shown above, wherein R$_1$ and R$_2$ are the same or wherein either R$_1$ or R$_2$, preferably R$_2$ are hydrogen.

Novel fluorinated carbocylic compounds that may be prepared in accordance with the present invention include substituted gem-dihalocyclohexane compounds exemplified by the formula

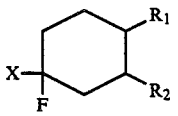

wherein X is chlorine or fluorine and R$_1$ and R$_2$ are independently selected from the group consisting of —H, —CH$_2$OH, —COF, —COCl, —CF$_3$, —CN,

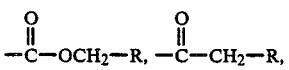

and —CH$_2$CH$_2$R, where R is —H or alkyl of 1-4 carbon atoms, with the proviso that at least one of R$_1$ and R$_2$ is other than —H.

The synthesis of the gem-dihalocyclohexane intermediates is accomplished by reaction of hydrogen fluoride with a chlorocyclohexenyl compound in a manner exemplified by the following equation.

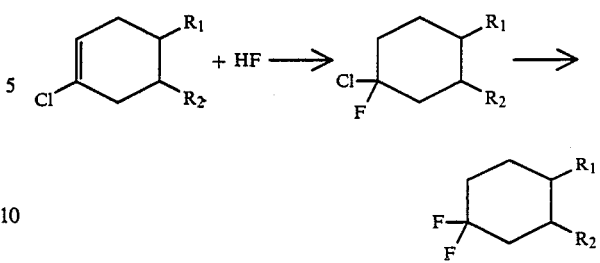

The reaction proceeds stepwise, and if pushed to completion will result in high yields of the gem-difluorocyclohexane compound. However, by appropriate limitation of time, temperature or hydrogen fluoride reactant, high yields of the chlorofluorocyclohexane compound may be recovered. Typical reaction products are a mixture of the two which may be conveniently separated, for example, by conventional physical separation techniques, such as fractional distillation, fractional crystallization, or the like. When the product is to be employed in the further preparation of fluorocyclohexenyl compounds, or fluoroaromatic compounds, such separation is not necessary, since either of these gem-dihalocyclohexane compounds may be employed for this purpose. The reaction of the chlorocylohexenyl compound with hydrogen fluoride is preferably carried out in the liquid phase, most preferably under reflux conditions. It is preferred to carry out the reaction neat, however, a solvent, for example diethyl ether, may be employed if desired.

The dehydrohalogenation reaction of the gem-dihalo intermediate(s) to form a fluorocyclohexenyl compound is exemplified by the following equation:

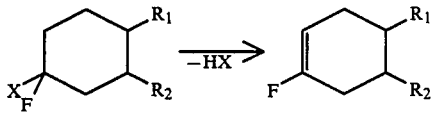

where X is Cl or F and R$_1$ and R$_2$ are as previously defined. It has been found preferable to remove excess hydrogen fluoride from the fluorination step, for example by vaporization, at the start or prior to the dehydrohalogenation step. The dehydrohalogenation step is preferably carried out in the vapor phase at atmospheric pressure, although sub-atmospheric or super-atmospheric conditions may be employed. The reaction may be carried out neat, however, it has been found that yields may be increased when a solvent such as a chlorinated aromatic solvent is employed. Suitable solvents include for example, monochlorobenzene, dichlorobenzene, trichlorobenzene, chloroxylenes, and the like. The temperature employed will depend on the boiling point of the solvent, but will typically be in the range of about 160° to about 460° Celsius and preferably in the range of about 240° to about 340° Celsius. The dehydrohalogenation reaction may be carried out at a lower temperature, such us about 200° Celsius when carried out in the presence of an alumina catalyst. However, the alumina catalyst serves preferentially as dehydrofluorination catalyst and thus is only recommended when the gem-dihalocyclohexane reactant is predominantly the gem-difluorocycloalkane. When an alumina catalyst is used in the presence of a chloro-fluorocyclohexane reactant, the formation of chloro-cyclohexenyl products is favored. When it is desired to drive the reaction in the direction of formation of the fluoroaromatic product directly, it is preferred to employ a dehydrogenation catalyst, such as a noble metal catalyst and the like.

The aromatization of the fluorocyclohexenyl intermediate is exemplified by the following equation:

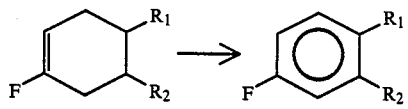

where $R_1$ and $R_2$ are as defined above. The reaction is carried out in the vapor phase in the presence of a dehydrogenation catalyst. Suitable dehydrogenation catalysts include, for example, platinum, palladium, rhodium, iridium, ruthenium, rhenium, or nickel metals, either in elemental form or as an M° compound or complex thereof, either unsupported or on a suitable support. Other suitable catalysts include copper chromite, which is believed to have the formula $CuO\cdot Cr_2O_3$, chromium oxide, molybdenum oxide, tungsten oxide, and vanadium oxide. Typical catalyst supports include for example activated carbon, charcoal, silicon carbide, silica gel, alumina, acidic silica-alumina, silica, titania, zirconia, kieselguhr, mixed rare earth oxides, carbonates, barium carbonate, barium sulfate, calcium carbonate, pumice, silica alumina mixtures, zeolites, and the like. Suitable catalytic complexes include the M° compounds where M is Pd, Pt, Ni, rhodium or ruthenium, and is bound in the structure by phosphine, phosphite or carbamyl ligands. Complexes of this type are generally soluble in the reaction mixtures employed in the process of this invention. Typical complexes include tetrakis(triphenylphosphine)platinum (O); Bis[bis(1,2-diphenylphosphino)ethane]palladium (O); Bis[bis(1,2-diphenylphosphino)benzene]palladium (O); Bis(1,5-cyclooctadiene)nickel (O); Tetrakis(triethylphosphite)nickel (O); Tetrakis(triphenylphosphine)nickel (O) and tetrakis(triphenylphosphite)nickel (O); chlorotris(triphenylphosphine)rhodium (I); and dichlorotris(triphenylphosphine)ruthenium (II). A preferred catalyst system is palladium on a carbon support. The reaction is generally carried out at a temperature of about 200° to about 400° and preferably about 250° to about 350° Celsius.

The aromatization reaction may be carried out neat. However, it has been found preferable to carry out the reaction in the presence of a solvent, preferably a halocarbon solvent which may serve as a hydrogen acceptor.

The hydrogen acceptors which may be employed in the aromatization step of this invention include those materials known in the art as hydrogen acceptors in like reactions. For example, the hydrogen acceptors include olefins containing 2 to 20 carbon atoms, aromatic nitrocompounds such as nitrobenzene, certain carbonyl compounds such as aldehydes and ketones, and certain halocarbon compounds capable of exchanging at least one chlorine, bromine, or iodine atom per molecule for a hydrogen atom. Preferred hydrogen acceptors for this purpose are halocarbons of the formula:

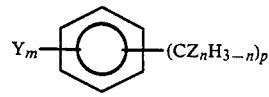

where Y is Cl, Br or I; Z is Cl, Br or I; m is 0 to 4; n is 0 to 3, p is 0 to 3, and m+n is at least 1; with the proviso that when m is 0, p is at least 1. Suitable halocarbon hydrogen acceptors are chloro-, bromo-, and iodoaromatic wherein the chloro-, bromo-, or iodo-, substituent is present either on the aromatic ring or on a side-chain such as an alkyl or alkoxy side-chain, including, for example, halobenzenes such as chlorobenzene, dichlorobenzene, trichlorobenzene, tetrachlorobenzene, bromobenzene, dibromobenzene, tribromobenzene, tetrabromobenzene; chlorotoluenes such as orthochlorotoluenes, orthobromotoluenes, dibromotoluene, tribromotoluene, tetrabromotoluene orthoiodotoluene, metaiodotoluene, paraiodotoluene, diiodotoluenes, triiodotoluenes, tetraiodotoluenes; benzylchlorides, such as 2-chlorobenzene chloride, 2,6-dichlorobenzylchloride, 2,3,6-trichlorobenzychloride, benzalchlorides, benzotrichloride, benzylbromide, benzalbromide, benzotribromide, benzyliodide, orthochlorobenzotrichloride, parachlorobenzotrichloride, parachlorobenzotrifluoride, various halogenated fused ring aromatics, such as the haloaphthalenes and haloanthracenes, wherein the halo is chloro, bromo or iodo.

The following examples are provided to further illustrate this invention and the manner in which it may be carried out. It will be understood, however, that the specific details given in the examples have been chosen for purposes of illustration and are not to be construed as a limitation on the invention. In the examples, unless otherwise indicated, all parts and percentages are by weight and all temperatures are in degrees Celsius.

EXAMPLE 1

Preparation of 1-chloro-4-carbomethoxy cyclohexane

A mixture of 200 parts of anhydrous aluminum chloride in 2000 parts of methylene chloride was maintained under an atmosphere of nitroge while 129 parts of methyl acrylate was added over a period of about 0.5 hours. With the addition of the methyl acrylate, the temperature of the mixture rose exothermically to about 34° C. The mixture was cooled to about 22° C. and 132.8 parts of freshly prepared chloroprene was added slowly, with stirring over a period of about 1.5 hours. During the addition, the temperature rose slowly to reflux condition (about 40° C.). The reaction mixture was then maintained under a nitrogen atmosphere, with stirring, for about 16 hours at ambient conditions. The crude reaction product was then treated with 10% HCl, and washed with methylene chloride and distilled to yield an essentially pure mixture of 1-chloro-4-carbomethoxy cyclohexene (92%) and its isomer 1-chloro-5-carbomethoxy cyclohexene (8%).

EXAMPLE 2

Addition of HF to 1-chloro-4-carbomethoxy cyclohexene under autogenous conditions A mixture of 17.5 parts of 1-chloro-4-carbomethoxy cyclohexene and 40 parts of anhydrous hydrogen fluoride was cooled to about −5° C. and sealed in an autoclave. Over a one hour period, the autoclave was heated to about 60° C. The pressure was maintained at about 24 to 34 psig by venting when pressure reached 34 psig to lower to 24 psig. The conditions were maintained for a period of about 2 hours until the pressure stabilized, indicating the essential completion of the reaction. The reactor cooled to ambient temperature and purged with nitrogen to remove excess hydrogen fluoride. The reaction mixture was treated with acetone, and the solution neutralized with anhydrous NaHCO$_3$, and analyzed by gas chromatography/mass spectrometry methods, with the results shown in Table I below.

EXAMPLE 3

Addition of HF to 1-chloro-4-carbomethoxy cyclohexene at atmospheric pressure

A mixture of 19.21 parts of anhydrous hydrogen fluoride and 17.5 parts of 1-chloro-4-carbomethoxy-cyclohexene was maintained at about 1° C. with stirring for about 0.5 hours, then warmed to about 5° C. and maintained there at for about 2.5 hours. An additional 20.82 parts of hydrogen fluoride was added and the reaction mixture was warmed to reflux (26° C.) and maintained thereat for about 2 hours then allowed to cool to ambient temperature (20° C.) over a 16 hour period. Samples of the reaction mixture were drawn periodically and analyzed by gas chromatography/mass spectrometry methods with the results as shown in Table I below.

TABLE 1

REACTION OF HF WITH 1-CHLORO-4-CARBOMETHOXY CYCLOHEXANE

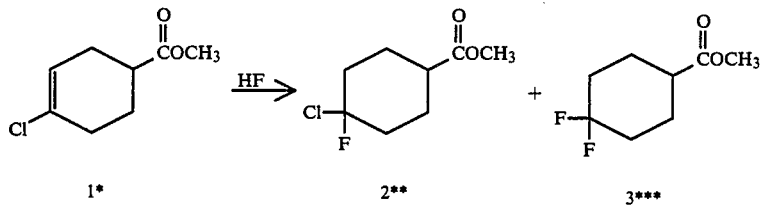

| MOLAR RATIO HF/ORGANIC | TEMP. | PRESSURE | TIME(HR) | PRODUCT DISTRIBUTION (GC AREAS IN %) | | | |
|---|---|---|---|---|---|---|---|
| | | | | 1 | 2 | 3 | Unwanted By-products |
| 20 | 60° C. | 29–34 PSIG | 3.5 | 3.5 | 0 | 82.7 | 13.6 |
| 9.6 | 1° C. | Atmospheric | 0.5 | 23 | 76 | 0 | 0 |
| 9.6 | 5° C. | Atmospheric | 2.5 | 6.5 | 92 | 0 | 0 |
| 20 | 26° C. | Atmospheric | 4.5 | 0 | 98 | 0.7 | 0.5 |
| 20 | 20° C. | Atmospheric | 21.5 | 0 | 47 | 37 | 10 |

*The starting material contained 8 percent of the isomer 1-chloro-5-carbomethoxy cyclohexene.
**The recovered product includes approximately 8% of the isomer gem-dihalo-3-carbomethoxy cyclohexane derived from the 1-chloro-5-carbomethoxy cyclohexene present in the starting material.

EXAMPLE 4

Synthesis of 1-fluoro-4-carbomethoxy-cyclohexene

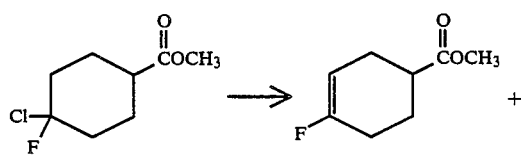

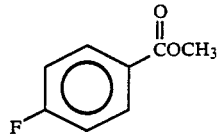

A mixture of 1.2 parts of 1-chloro-1-fluoro-4-carbomethoxy-cyclohexane and 4.8 parts of o-dichlorobenzene were added to a bed of 2% palladium on carbon maintained at 300° C. A stream of nitrogen at 400 cc/min. swept the products into two cold traps at 0° C. and −80° C. to yield 3.84 parts of combined products. Analysis by gas chromatography and mass spectrometry indicated complete reaction to yield 85% 1-fluoro-4-carbomethoxy-cyclohexane, 5% 1-chloro-4-carbomethoxy-cyclohexane and 10% methyl-4-fluorobenzoate, excluding the solvent.

EXAMPLE 5

Dehydrohalogenation of 1,1-difluoro-4-carbomethoxy-cyclohexane

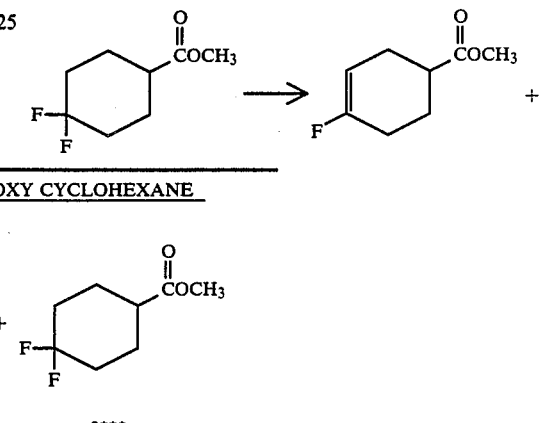

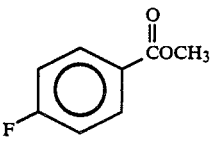

A mixture of 1.2 parts of 1,1-difluoro-4-carbomethoxy-cyclohexane and 4.8 parts of o-dichlorobenzene was added to a bed of 10 parts of 2% palladium on carbon at 280° C. A nitrogen gas purge at 280° C. swept the products into cold traps held at 0° C. and −80° C. to yield 4.2 parts of a mixture, consisting of 76% unreacted starting material, 19% 1-fluoro-4-carbomethoxycyclohexene and 5% methyl-4-fluorobenzoate, excluding the solvent.

EXAMPLE 6

Elimination of HX from 1-chloro-4-carbomethoxy-cyclohexene over alumina.

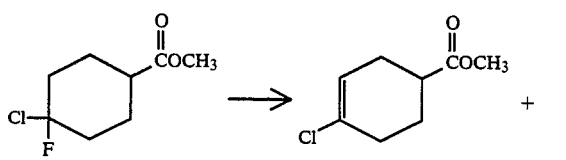

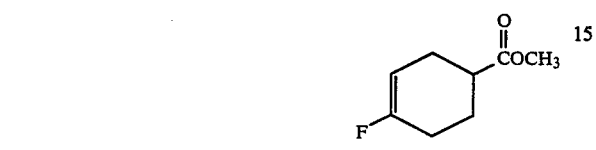

A mixture of 1.16 parts of 1-chloro-1-fluoro-4-carbomethoxycyclohexane, 20 parts of sulfolane and 2.25 parts of basic alumina were heated at 180° C. for 26 hours. The reaction product was analyzed directly by gas chromatography and mass spectrometry methods. Two products were obtained; 1-fluoro-4-carbomethoxy-cyclohexene and 1-chloro-4-carbomethoxycyclohexene in the ratio of 15/85.

EXAMPLE 7

Preparation of methyl-4-fluorobenzoate from 1-fluoro-4-carbomethoxycyclohexene.

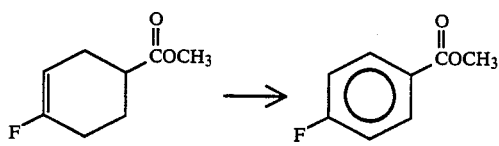

A mixture of 6.0 parts of 1-fluoro-4-carbomethoxycyclohexane and 24 parts of o-dichlorobenzene was added slowly to a bed of 100.1 parts of 2% palladium on carbon at 280° C. The vapors were swept into cold traps at 0° C. and −80° C. with a nitrogen stream at 60 cc/min. over a 2 hour period to yield 14.3 parts of product. The reaction product was a mixture of 61% unreacted starting material, 33% methyl-4-fluorobenzoate and 6% methyl benzoate, excluding the solvent.

EXAMPLE 8

Preparaion of methyl-4-fluorobenzoate from 1-chloro-1-fluoro-4-carbomethoxycyclohexane

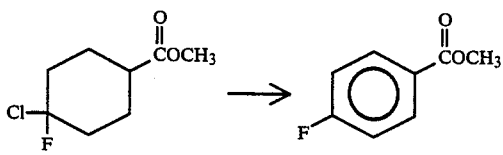

A mixture of 1.2 parts of 1-chloro-1-fluoro-4-carbomethoxycyclohexane and 4.8 parts of 2,4-dichlorobenzylchloride were added slowly to a bed of 9.35 parts of 2% palladium on carbon (4–8 mesh) at 280° C. The vapor was swept into two traps of 0° C. and −80° C. with a N₂ stream of 60 cc/min. Combined yield from both traps was 1.02 parts of product which consisted of 26% methyl-4-fluoro-benzoate, 62% 1-fluoro-4-carbomethoxycyclohexene and 10% 1-chloro-4-carbomethoxycyclohexene. Analysis was done by gas chromatography and mass spectrometry methods. bed of 100.1 parts of 2% palladium on carbon at 280° C. The vapors were swept into cold traps at 0° C. and −80° C. with a nitrogen stream at 60 cc/min. over a 2 hour period to yield 14.3 parts of product. The reaction product was a mixture of 61% unreacted starting material, 33% methyl-4-fluorobenzoate and 6% methyl benzoate, excluding the solvent.

EXAMPLE 8

Preparation of methyl-4-fluorobenzoate from 1-chloro-1-fluoro-4-carbomethoxycyclohexane

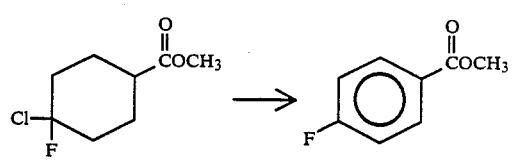

A mixture of 1.2 parts of 1-chloro-1-fluoro-4-carbomethoxycyclohexane and 4.8 parts of 2,4-dichlorobenzylchloride were added slowly to a bed of 9.35 parts of 2% palladium on carbon (4–8 mesh) at 280° C. The vapor was swept into two traps of 0° C. and −80° C. with a N₂ stream of 60 cc/min. Combined yield from both traps was 1.02 parts of product which consisted of 26% methyl-4-fluoro-benzoate, 62% 1-fluoro-4-carbomethoxycyclohexene and 10% 1-chloro-4-carbomethoxycyclohexene. Analysis was done by gas chromatography and mass spectrometry methods.

EXAMPLE 9

Preparation of 4-fluoroacetophenone from chloroprene and methyl vinyl ketone

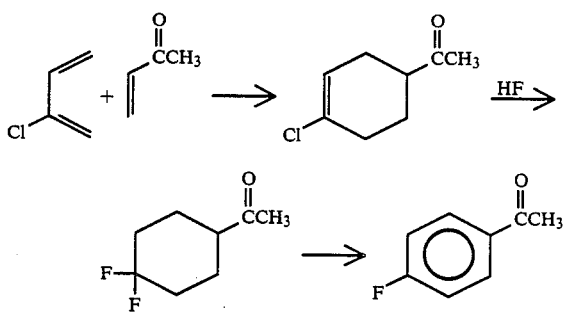

(a) Synthesis of 1-chloro-4-acetylcylohexene

To a solution of 98.1 parts of methyl vinyl ketone, 187 parts of anhydrous aluminum chloride and 1980 parts of methylene chloride was added 123 parts of chloroprene and the mixture was stirred at 25° C. for three hours and left standing for another 16 hours. Water was added to the reaction mixture and the organic layer was washed with 5% hydrochloric acid. Distillation gave a center cut of 61 parts of 1-chloro-4-acetyl-cyclohexene (125°-6° C./20 mm Hg). Reference: A. A. Petrov and N. P. Sopov, CA 42, 1910h (1948).

(b) Preparation of 1,1-difluoro-4-acetylcyclohexane

To 44.3 parts of 1-chloro-4-acetylcyclohexane was added 59.5 parts of anhydrous hydrogen fluoride at 11°

C. The solution was allowed to reflux at 24° C. for 3 hours and then left standing for 16 hours while purging with a nitrogen flow which slowly removed HF from the reaction mixture. The reaction product was dissolved in 30 parts of acetone and sodium bicarbonate was added until the evolution of CO₂ ceased. The solution was dried with Na₂SO₄ and concentrated to give 39.1 parts of crude product. Distillation on a spinning band column gave a center cut of 20.63 parts of the pure product, 1,1-difluoro-4-acetylcyclohexane (bp. 84° C./13 mm Hg).

(c) Preparation of 4-fluoroacetophenone

A mixture of 2 parts of 1,1-difluoro-4-acetylcyclohexane and 8 parts o-dichlorobenzene was added to a bed of 11.4 parts 2% palladium on carbon at 300° C. The products were swept into traps at 0° C. and −80° C. with a nitrogen flow of 50 cc/min. to yield 8.5 parts product in the 0° C. trap after 1.5 hours. The product was neutralized with sodium bicarbonate, dried over sodium sulfate and filtered to yield a clear solution of product in o-dichlorobenzene solvent. Analysis by gas chromatography/mass spectrometry indicated 49% conversion to products and 32% of the product mixture was 4-fluoroacetophenone.

EXAMPLE 10

Preparation of 1-chloro-4,5-dicarbomethoxy cyclohexene

Twenty parts of 4-chlorotetrahydrophthalic anhydride was hydrolyzed with aqueous NaOH to form the corresponding di-acid. Approximately 6 parts of the di-acid was reacted quantitatively with diazomethane to yield 7.2 parts of 1-chloro-4,5-dicarbomethoxycyclohexene.

EXAMPLE 11

Preparation of 1,1-dihalo-3,4-di-carbomethoxy cyclohexane

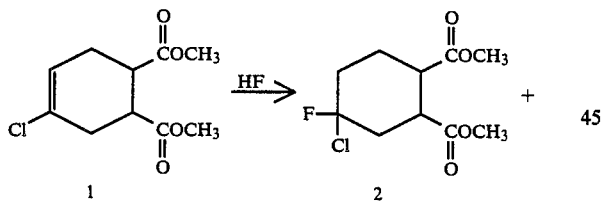

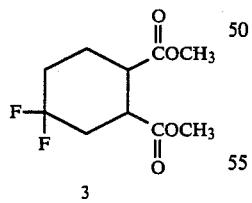

A mixture of 3.5 parts and 4.8 parts of anhydrous hydrogen fluoride was maintained at a temperature of 0° to 17° C., with stirring, for about 3 hours. The mixture was then warmed to reflux condition (27°–28° C.) and maintained thereat for about 4 hours. The reaction mixture was then purged overnight with nitrogen then treated with acetone, neutralized with sodium bicarbonate, dried over sodium sulfate and filtered. The acetone was removed by evaporation. Analysis of the product by gas chromatography/mass spectrometry indicated 37% of the 1-chloro-4,5-dicarbomethoxy starting material (1), 54% 1-chloro-1-fluoro-3,4-dicarbomethoxy cyclohexane and 4.3% of 1,1-difluoro-3,4-dicarbomethoxy cyclohexane and 3.7% impurities.

What is claimed is:

1. A gem-dihalocyclohexane compound of the formula

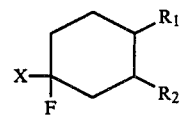

wherein X is chlorine or fluorine and R₁ and R₂ are independently selected from the group consisting of —H, —CH₂OH, —COF, —COCl, —CF₃, —CN,

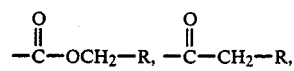

and —CH₂CH₂R, wherein R is —H or alkyl of 1–4 carbon atoms; with the proviso that at least one of R₁ and R₂ is other than —H.

2. A compound according to claim 1 wherein X is chlorine.

3. A compound according to claim 1 wherein X is fluorine.

4. A compound according to claim 1 wherein R₁ and R₂ are the same.

5. A compound of the formula

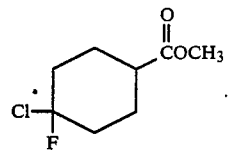

6. A compound of the formula

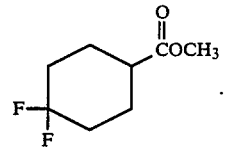

7. A compound of the formula

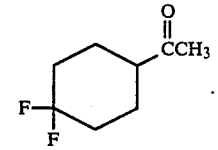

8. A compound of the formula

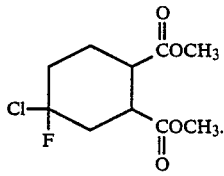

9. A compound of the formula

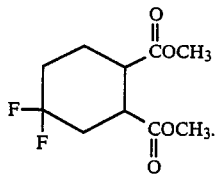

10. A gem-dihalocyclohexane compound of the formula

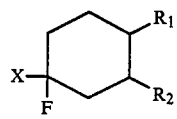

wherein X is chlorine or fluorine and $R_1$ is —H and $R_2$ is selected from the group consisting of —$CH_2OH$, —COF, —$CF_3$, CN, $$-\overset{O}{\underset{\|}{C}}-OCH_2-R, \quad -\overset{O}{\underset{\|}{C}}-CH_2-R,$$

and —$CH_2CH_2R$, wherein R is —H or alkyl or 1-4 carbon atoms.

11. A gem-dihalocyclohexane compound of the formula

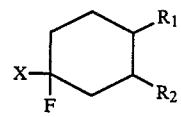

wherein X is chlorine or fluorine and $R_1$ is selected from the group consisting of —$CH_2OH$, —COF, —COCl, —$CF_3$, —CN, $$-\overset{O}{\underset{\|}{C}}-OCH_2-R, \quad -\overset{O}{\underset{\|}{C}}-CH_2-R,$$

and —$CH_2CH_2R$, wherein R is —H or alkyl or 1-4 carbon atoms and $R_2$ is H.

* * * * *